(12) United States Patent
Kuo (10) Patent No.: US 7,942,672 B2
(45) Date of Patent: May 17, 2011

(54) GINGIVA MODELING

(75) Inventor: Eric E. Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 624 days.

(21) Appl. No.: 12/070,140

(22) Filed: Feb. 15, 2008

(65) Prior Publication Data

US 2009/0208897 A1 Aug. 20, 2009

(51) Int. Cl.
*A61C 3/00* (2006.01)
(52) U.S. Cl. .......................................... 433/215; 700/98
(58) Field of Classification Search .................... 433/24, 433/72, 215, 229; 600/589, 590; 33/513, 33/514; 700/98
See application file for complete search history.

(56) References Cited

U.S. PATENT DOCUMENTS

| | | | | |
|---|---|---|---|---|
| 5,318,442 | A * | 6/1994 | Jeffcoat et al. | 433/72 |
| 6,514,074 | B1 | 2/2003 | Chishti et al. | |
| 6,739,870 | B2 * | 5/2004 | Lai et al. | 433/24 |
| 7,040,896 | B2 | 5/2006 | Pavlovskaia et al. | |
| 2003/0039941 | A1 * | 2/2003 | Chishti et al. | 433/24 |
| 2004/0081938 | A1 * | 4/2004 | Chishti et al. | 433/24 |
| 2008/0026340 | A1 * | 1/2008 | Gerlach et al. | 433/29 |

OTHER PUBLICATIONS

Bourauel et al., "Simulation of orthodontic tooth movements A comparison of numerical methods", 1999, Journal of Orofacial Orthopedics/Fortschritte der Kieferorthopädie, vol. 60, No. 2, 136-151.*
Cattaneo et al., "The Finite Element Method: a tool to study orthodontic tooth movement", 2005, Journal of Dental Research, vol. 84, No. 5, 423-433.*
Natali et al., "Numerical analysis of tooth mobility: formuation of non-linear constitutive law for the periodontal ligament", 2004, Dental Materials, vol. 20, 623-629.*
Puente et al., "Initial stress differences between tipping and torque movements. A three-dimensional finite element analysis", 1996, European Journal of Orthodontics, vol. 18, 329-339.*

* cited by examiner

*Primary Examiner* — Cris L Rodriguez
*Assistant Examiner* — Michael R Ballinger
(74) *Attorney, Agent, or Firm* — Brooks, Cameron & Huebsch, PLLC (57) ABSTRACT

Embodiments are provided for modeling gingiva. One method embodiment includes scanning a patient's teeth and gums, or a physical model thereof, to obtain location data, developing a digital model via a computing device, where the model represents a dentition and gingiva from the location data, defining in the model a gingival line at an intersection between at least one tooth and at least a portion of its surrounding gums, measuring a gingival pocket depth at a number of reference locations, and establishing in the model one or more gingival attachment points at the pocket depth from the gingival line.

19 Claims, 11 Drawing Sheets

Fig. 12

GINGIVA MODELING

BACKGROUND

The present disclosure is related generally to the field of dental treatment. More particularly, the present disclosure is related to methods, devices, and systems for dynamically remodeling virtual gingival tissue to better accommodate gingival tissue changes from orthodontic tooth movement, changes in oral hygiene, periodontal surgery, dental compression, and/or dental eruption, among other changes.

Many dental treatments involve repositioning misaligned teeth and changing bite configurations for improved cosmetic appearance and dental function. Orthodontic repositioning can be accomplished, for example, by applying controlled forces to one or more teeth over a period of time. Through repositioning and other changes that can take place in an individual's mouth, the contour of the gingiva can change.

An example of orthodontic repositioning that can occur can be through a dental process that uses positioning appliances for realigning teeth. Such appliances may utilize a thin shell of material having resilient properties, referred to as an "aligner" that generally conforms to a patient's teeth but is slightly out of alignment with the initial tooth configuration.

Placement of such an appliance over the teeth can provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth. As the teeth move, and/or other changes occur, the contour of the gingival tissue surrounding the teeth may change. Additionally, the junction between the gingiva and the tooth (the "gingival line") can change.

Some appliances may be designed according to a model of a patient's gingival line, where the gingival line is associated with a cut line of the appliance. When the gingival line changes, the appliance may not fit as originally designed with respect to the gingiva. Such fit may potentially lead to reduced aligner aesthetics, poorer device adaptation to the teeth, and/or decreased performance, for example.

DETAILED DESCRIPTION

Embodiments of the present disclosure include method, device, and system embodiments for modeling gingiva. For example, the embodiments include, a computing device implemented method for scanning a patient's teeth and/or gums, or a physical model thereof, to obtain location data, developing a digital model via a computing device, where the model represents a dentition and gingiva from the location data, defining in the model a gingival line at an intersection between at least one tooth and at least a portion of its surrounding gums, measuring a gingival pocket depth at a number of reference locations, and establishing in the model one or more gingival attachment points at the pocket depth from the gingival line. Such embodiments can better accommodate gingival tissue changes to provide better appliance adaptation, which may yield better appliance aesthetics and/or performance, in some instances.

Some embodiments can include computing device executable instructions to receive location data obtained from a scan of a patient's teeth and/or gums, or a physical model thereof, develop a digital model representing a dentition and/or gingiva from the location data, define in the model a gingival line at an intersection between at least one tooth and at least a portion of its surrounding gums, receive distance data obtained from a measurement of gingival pocket depth at a number of reference locations, and establish in the model a gingival attachment point at the pocket depth from the gingival line. This can be beneficial in providing more accurate modeling, which may yield a more precise fit for orthodontic appliances over time than using a static modeling system, in some instances.

Figure 1:
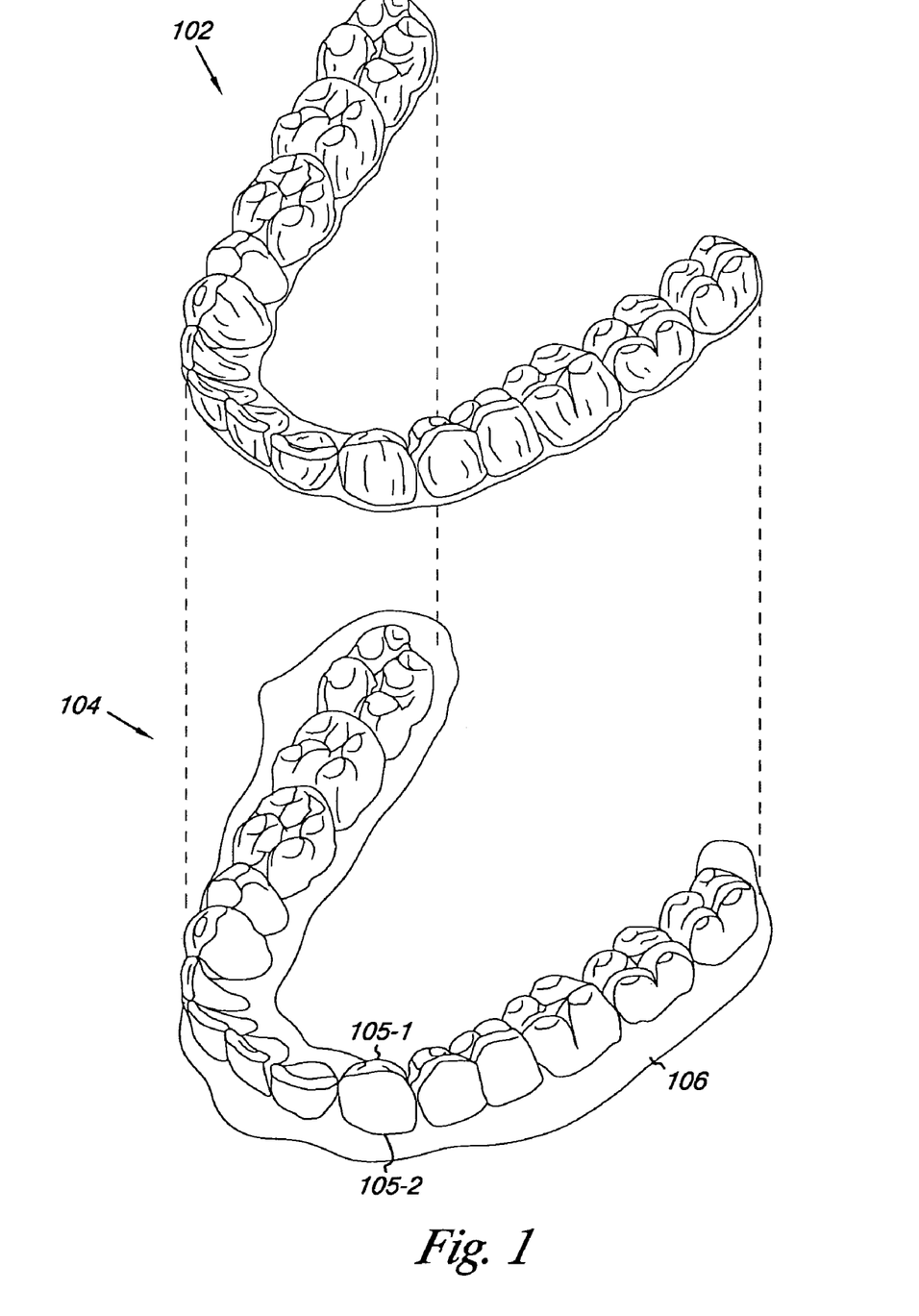
FIG. 1 illustrates a dental position adjustment appliance being applied to a set of teeth.

FIG. 1 illustrates a dental position adjustment appliance 102 being applied to a set of teeth 104 according to embodiments of the present disclosure. Appliances according to the present disclosure can include, in some embodiments, a plurality of incremental dental position adjustment appliances. The appliances, such as appliance 102 illustrated in FIG. 1, can be utilized to affect incremental repositioning of individual teeth in the jaw, among other suitable uses.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance (e.g., appliance 102 in FIG. 1) can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth 104 present in the upper and/or lower jaw.

Each "tooth" in the shell may be designed to span from a first visible end 105-1 of a patient's tooth (e.g., the cusp) to a second visible end 105-2 of the patient's tooth approximately at the gingival line (e.g., gum line). Such a design can provide an aesthetically pleasing appearance, for example, when the shell is optically transparent and covers at least the front face of a patient's tooth. That is, the appliance may not be visible at first glance when it spans from the top visible portion to bottom visible portion of the patient's teeth.

However, as a patient's treatment progresses, the visible distance from the first end 105-1 of the patient's tooth opposite the gingival line to the second end 105-2 of the patient's tooth approximately at the gingival line (the "clinical crown" of a tooth) can change. Such a change can cause the previously manufactured appliance to not properly fit as estimated when it was manufactured (e.g., allowing the appliance to be more easily noticed at first glance due to a distance between the edge of the aligner and the gingival line).

In some embodiments, instructions can be executed to create a model representing a dentition and/or gingiva including one or more defined gingival lines and/or gingival attachment points. This model may be used to create a treatment plan and/or a set of appliances (e.g., appliance 102 in FIG. 1) for placement over one or more teeth. In some embodiments, one or more computing device models described herein can be used to form an appliance and/or set of appliances that are more aesthetically pleasing and/or more effective by providing appliances formed to accurately fit the patient's teeth.

Using computing device models described herein, a dental professional can create a set of appliances that account for relative changes to the patient's dentition and gingiva during a course of treatment. For example, as the contours of the patient's gingival line change during treatment, a successive appliance may be used that has been designed to account for such change based on changes to the virtual gingival line according to the computing device model created at or near the onset of treatment. This may be a percentage of initial distance/contour change, an incremental distance/contour change, or a non-linear distance/contour change over time and/or over a number of aligners, for example.

In addition to the benefits described above, some embodiments of the present disclosure can be used to provide a more accurately fitting appliance that can benefit the patient through improved treatment functionality. For example, an appliance and/or set of appliances that fit the patient's teeth more accurately can allow for more efficient repositioning of the patient's teeth.

As a clinical crown becomes more visible, for example, better adaptation to the exposed surfaces can better enable aligner adaptation to the tooth in order to deliver orthodontic forces. If a clinical crown becomes less visible due to enlargement of the gingival contour, improved avoidance of the gingiva by the appliance edge can help prevent patient discomfort, which may affect the patient's ability to wear the device as instructed. An example of bunching, as will be discussed below, may be the movement of two teeth towards each other whereby closure of the space between two teeth (e.g., a diastema) can lead to the compression of the gingival tissue therebetween.

One method of emulating gingival tissue is to create virtual attachments of the virtual gingiva to the virtual teeth, then to position the tissue based on the attachment points during tooth movement simulation. The gingival connection points on the teeth can remain constant such that from stage to stage the gingiva remodels on the computing device in a fashion that is similar to the way the gingiva remodels in actuality.

Rather than connecting various attachment points to the visible gingival line at the time of impression to create an attachment level, one or more embodiments of the present disclosure attach the virtual gingiva to the cementoenamel junction (CEJ) of the tooth root. The CEJ is where the gingiva often attaches to the tooth via periodontal fibers.

With respect to scanning a patient's teeth and gums, or a physical model thereof, to obtain location data, this location data can be for the positions of the teeth with respect to the other features of the mouth, for obtaining positional information about the gingiva such as the visible gingival line and/or one or more points of attachment of the gingiva to one or more teeth, and/or a pocket depth at one or more points around one or more teeth.

This information can then be used to develop a digital model (e.g., via a computing device). The model, for example, can include a representation of a dentition and/or gingiva from the location data which can, for example, be used to provide a visual model on a display for viewing by a treatment professional.

In some embodiments, the model includes a gingival line defined at an intersection between at least one tooth and at least a portion (e.g., one or more attachment points where the gingiva attaches to the tooth, such as at the CEJ) of its surrounding gums (i.e., gingiva). In some embodiments, the gingival pocket depth can be measured at a number of reference locations.

This can be done manually by probing the pocket depth with a probe or through use of an automated data collecting method, such as by scanning or the like. This information can be used to provide more information about the shape of the gingiva for purposes of providing more accurate modeling of the movement of teeth and/or gingiva, among other benefits. The information can be useful, for example, in establishing, in a virtual model, one or more gingival attachment points (e.g., at or near the bottom of the pocket) at the pocket depth from the gingival line (e.g., at or near the top of the pocket).

This attachment level may be determined by periodontal probing by a dental professional. Accordingly, one or more embodiments of the present disclosure can employ the use of one or more automatic determinations of the gingival pocket measurement (e.g., bone level) through various scanning mechanisms such as CT, MRI, X-Ray, etc.

If orthodontic treatment of a patient results in relatively slow movement of the teeth, the periodontal fibers that connect from the periodontium to the teeth can remain attached to the tooth and the contour of the gingiva itself may remodel as the teeth move. That is, the attachment points of the tissue to the teeth remains in the same place on the teeth as the teeth move. In contrast, the gingival cusp (e.g., top of the gum line) can change even when the attachment of tissue to the teeth remains in the same place from stretching or bunching as the tooth moves.

Thus, according to one or more embodiments of the present disclosure, accurate cut lines for a set of appliances may be realized by better modeling the gingiva as described herein. Accurate cut lines may be realized by decoupling the cut line from the gingival line altogether.

That is, the appliance may have a cut line determined by modeling the gingival line dynamically as opposed to statically. For example, in cases where the root of a patient's tooth may be exposed, one or more embodiments of the present disclosure can provide an appliance cut line such that the crown of the tooth can be covered, but the appliance may not extend to cover the root of the tooth.

Figure 2:
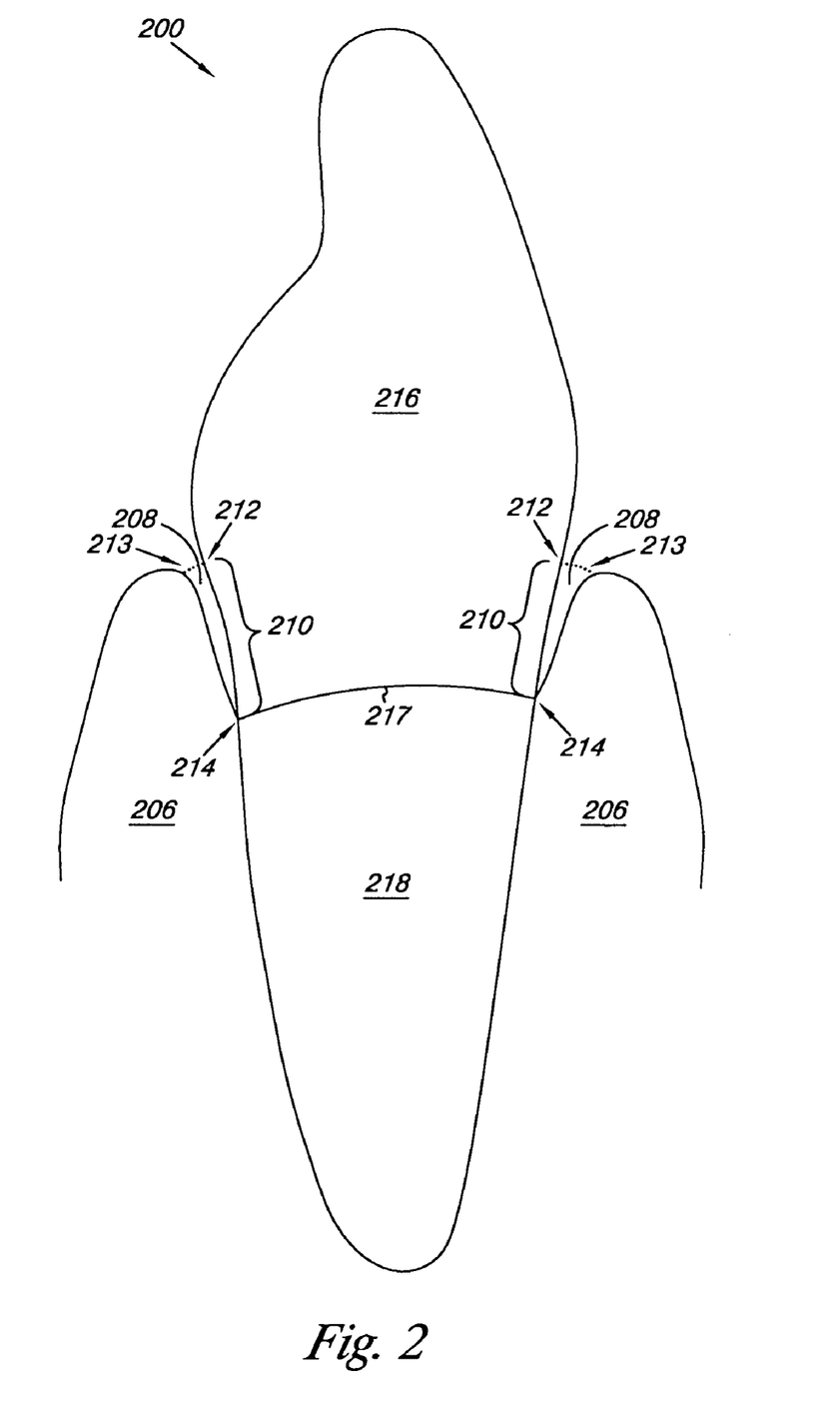
FIG. 2 illustrates a virtual model of a tooth according to one or more embodiments of the present disclosure.

FIG. 2 illustrates a virtual model of a tooth according to one or more embodiments of the present disclosure. The model of tooth 200 includes gingival lines 213 and gingival attachment points 214. A gingival attachment point is the point on the tooth where the gingiva (e.g., gums 206) connects to the tooth.

As one of ordinary skill in the art will appreciate, the gingival attachment point 214, on an actual tooth, can be located at or near the CEJ 217. The model of tooth 200 includes a crown 216 and root 218 separated by the CEJ 217.

The model of tooth 200 also includes a gingival point 212, which is the point on the tooth where the top of the gingiva contacts, or appears to contact the model of tooth 200. That is, the gingival point 212 marks the gum line on the model of tooth 200.

Computing device models, according to some previous approaches, use gingival point 212 as a reference for modeling dentition and gingiva and/or for creating appliances, such as appliance 102 in FIG. 1. In contrast, one or more embodiments of the present disclosure can use gingival attachment points 214 as references (e.g., control points) for modeling dentition and gingiva and/or for forming appliances.

Between the model of tooth 200 and gingiva 206 is a pocket 208 that extends from the gingival point 212 to the gingival attachment point 214. The depth 210 of the pocket 208 can be an indication of the health of the gingiva where, for example, a shallower pocket generally indicates better health.

The model of tooth 200 is surrounded by gingiva (e.g., gums) 206. The gingiva are separated from the outer portions of the model of tooth 200 (e.g., buccal/facial and lingual surfaces) by pockets 208. When viewed facially, a series of gingival points 212 can form a gingival line (e.g., gingival line 213).

One or more computing device modeling embodiments of the present disclosure may use gingival attachment points 214 to model dentition and gingiva. Such embodiments can be useful, for example, to compensate for changes in the patient's gingiva during treatment by providing a more accurately fitting appliance.

Figure 3A:
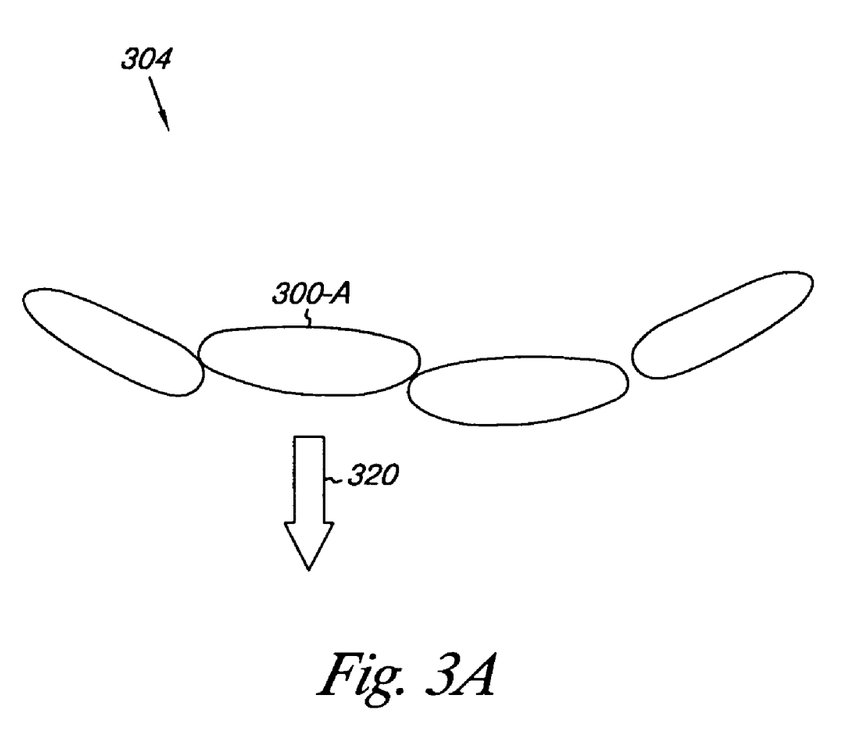
FIG. 3A illustrates a virtual model including a misaligned tooth being aligned with several teeth according to one or more embodiments of the present disclosure.

FIG. 3A illustrates a virtual model including a misaligned tooth 300-A being aligned with several teeth 304 according to one or more embodiments of the present disclosure. The model of teeth 304 illustrated in FIG. 3A is viewed from an occlusal perspective.

A misaligned tooth, such as the model of a misaligned tooth 300-A, may be aligned by applying a force to the tooth (e.g., via an appliance such as appliance 102 in FIG. 1). As appropriate force is applied to the tooth, it can transition in a direction 320 to become aligned with the other teeth 304. Computing device models, according to one or more embodiments of the present disclosure, can simulate forces, and the effects of such forces, on model teeth (e.g., model tooth 300-A) and the virtual gingiva.

Figure 3B:
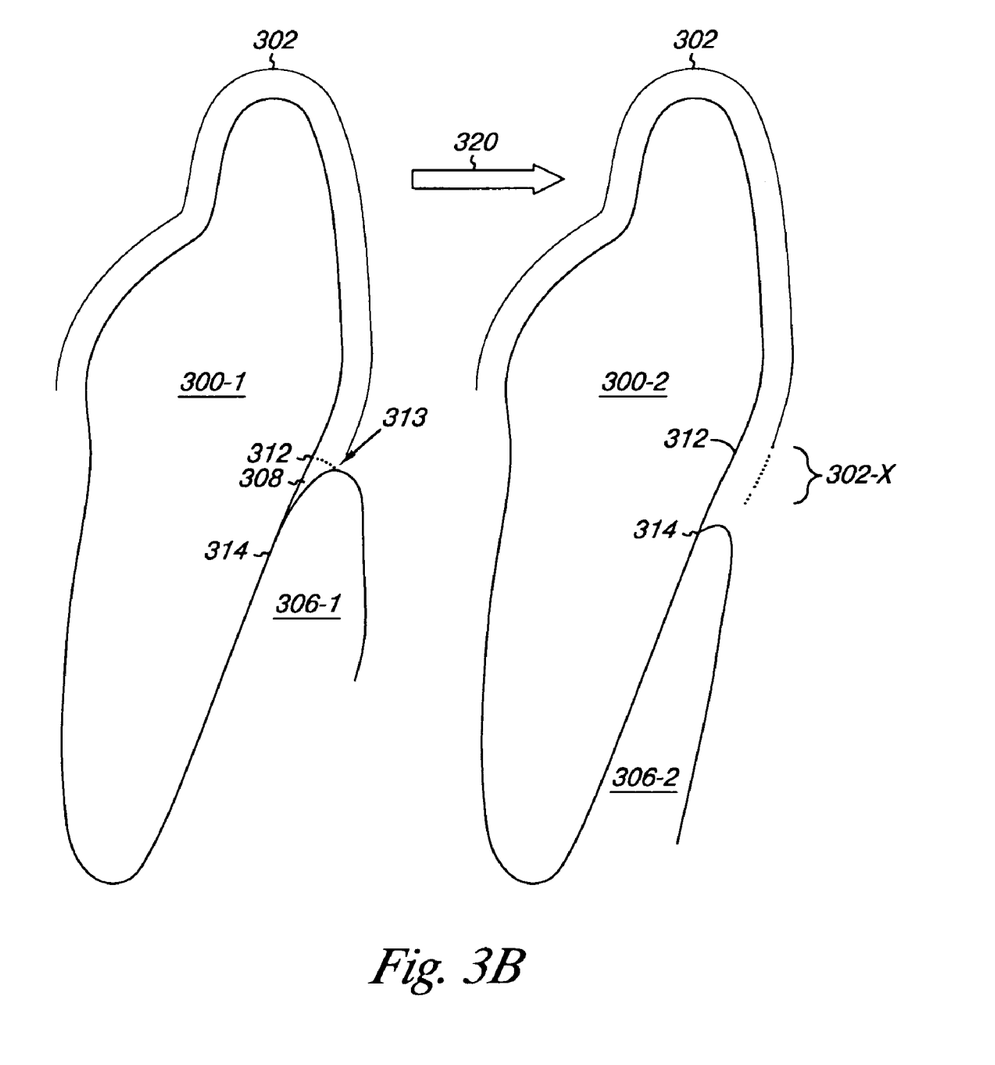
FIG. 3B illustrates a virtual model of a change in gingival tissue as the misaligned tooth of FIG. 3A is aligned according to one or more embodiments of the present disclosure.

FIG. 3B illustrates a virtual model of a change in gingival tissue as the misaligned tooth 300-A of FIG. 3A is aligned using an appliance 302 according to one or more embodiments of the present disclosure. The proximal perspective of tooth 300-1 illustrated on the left side of FIG. 3B represents misaligned tooth 300-A in FIG. 3A before it transitions in response to an applied force.

The model of tooth 300-1 is illustrated adjacent to a first gingival position 306-1 including a gingival line 313 with a gingival point 312. The gingiva attaches to the virtual tooth 300-1 at gingival attachment point 314. The space between the first gingival position 306-1 and virtual tooth 300-1 is illustrated as pocket 308.

After the model of tooth 300-1 moves 320, it is illustrated as virtual tooth 300-2. As the virtual tooth moves forward, the tissue (e.g., gingiva) can become taut as shown by the second gingival position 306-2. Such a change can also reduce the depth of the pocket 308.

In some embodiments an expected deformation of gum tissue surrounding a particular tooth can be derived based on force (e.g., a tension force) applied to the gum tissue through one or more gingival attachment points. In one or more embodiments the force applied through one or more gingival attachment points is transmitted from a positioning force applied to the particular tooth. For example, the force applied to the particular tooth can be a virtual positioning force from a simulated dental treatment plan.

As the virtual tooth moves, the gingiva remains attached at gingival attachment point 314, but the gingiva can stretch from the first gingival position 306-1 to the second gingival position 306-2 at least partially in response to the movement of the virtual tooth 300-2. While the gingival attachment point 314 remains in the same location on the tooth, the top "crest" of the gingiva is at a lower point with respect to the tooth. That is, more of the virtual tooth 300-2 crown is facially visible above the gum line than that of virtual tooth 300-1 leaving an uncovered portion 302-X of the tooth.

Since the tooth positioning appliance may be fabricated based on the original gingival line presented, such an uncovered portion 302-X can be aesthetically unpleasing, in some instances, in that an otherwise unnoticed appliance 302 can become readily apparent due to the observable difference between the tooth and appliance at the boundary therebetween. The uncovered portion 302-X can also allow various inefficiencies in the performance of the appliance 302, for example, because a portion 302-X of the tooth that would otherwise be available for applying one or more forces is not contacted by the appliance 302, in some instances.

Figure 4A:
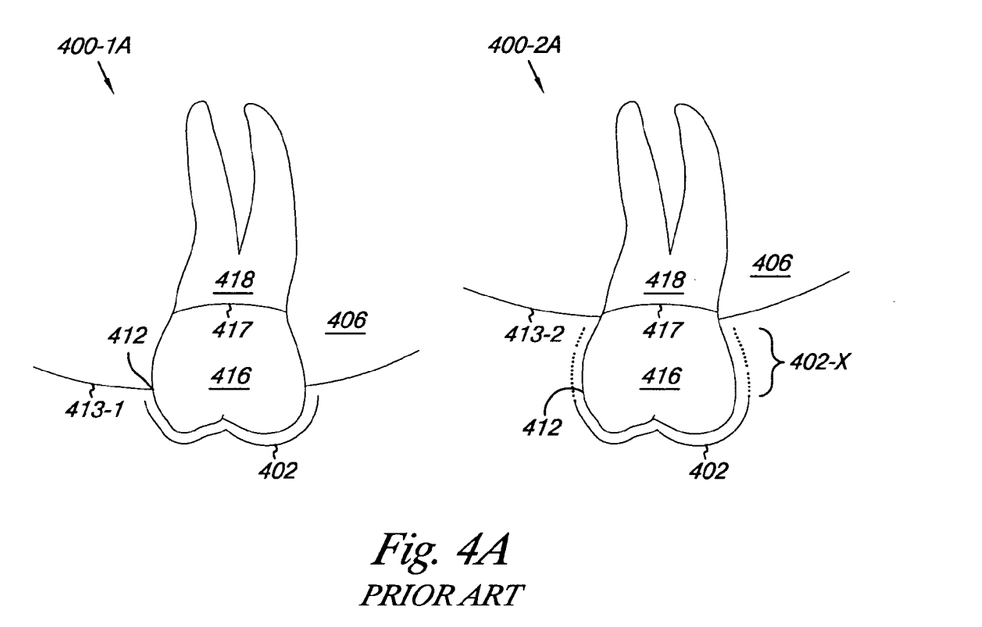
FIG. 4A illustrates a prior art model of a tooth when the tooth is partially erupted and fully erupted.

FIG. 4A illustrates a prior art model of a tooth when the tooth is partially erupted 400-1A and fully erupted 400-2A. The model of partially erupted tooth 400-1A includes an appliance 402 that covers the occlusal surface of the virtual tooth 400-1A and approaches the gingival line 413-1. The tooth models 400-1A and 400-1B includes a crown 416 and root 418 separated by the CEJ 417.

Virtual tooth 400-1A, as partially erupted from the gingiva 406, has a gingival point 412 where the gingival line 413-1 meets the crown 416. An appliance 402 is illustrated as using gingival point 412 as a reference.

After the tooth fully erupts, as simulated by virtual tooth 400-2A, the gingival line 413-2 meets the tooth near the CEJ 417. However, some previous computing device models would still rely on gingival point 412 as a reference, and thus appliance 402 formed according to such models may leave a portion 402-X of the tooth 400-2A uncovered.

Figure 4B:
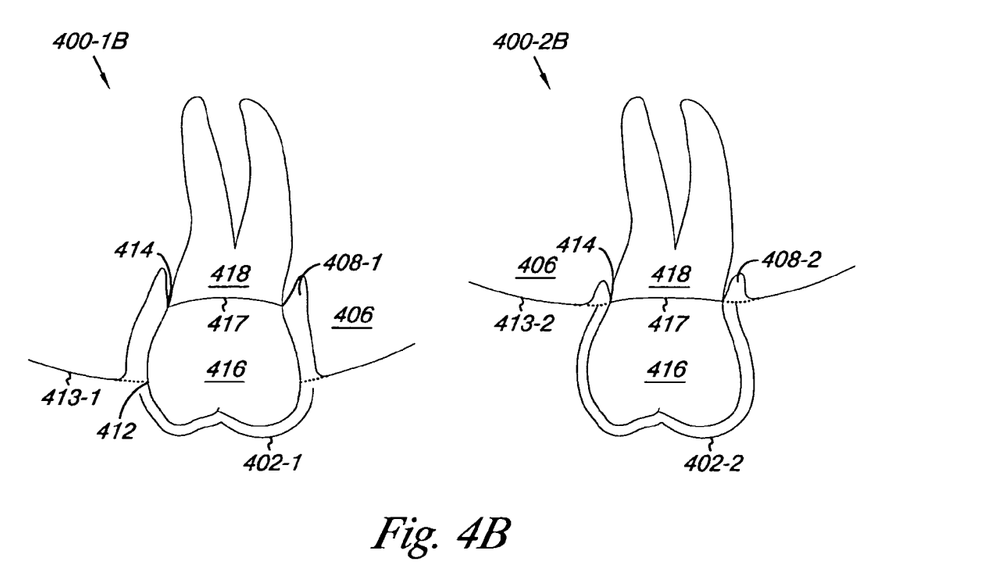
FIG. 4B illustrates a virtual model of a tooth when the tooth is partially erupted and fully erupted according to one or more embodiments of the present disclosure.

FIG. 4B illustrates a virtual model of a tooth when the tooth is partially erupted 400-1B and fully erupted 400-2B according to one or more embodiments of the present disclosure. The models of the partially erupted tooth 400-1B and fully erupted tooth 400-2B include gingival attachment points 414 and an appliance (e.g., appliance 402-1). The tooth models 400-1A and 400-1B includes a crown 416 and root 418 separated by the CEJ 417.

The model of tooth 400-1B, created according to one or more embodiments of the present disclosure includes a deviation from the first gingival line 413-1 to form a gingival attachment point 414 and simulated pocket 408-1 in the gingival tissue 406. The gingival point 412 is illustrated to indicate an approximate length of an appliance 402-1 that can be formed, for example, at this stage.

The virtual gingival attachment 414 can be placed at pocket depth if the actual pocket depth can be measured. In some embodiments, the gingival attachment 414 can alternatively be placed at the CEJ 417 (e.g., if the pocket depth cannot be measured). As the modeling process simulates eruption of tooth 400-1B (e.g., tooth 400-2B), the gingival attachment 414 can be maintained, but the gingival tissue 406 around it can be stretched and/or everted as indicated by reduced pocket 408-2 and second gingival line 413-2.

The slack from the reduced pocket 408-2 can allow, for example, a more accurate representation of the gingival tissue 406 following the eruption, in some instances. Accordingly, per one or more embodiments of the present disclosure, based upon the more accurate representation, a better fitting appliance 402-2 can be modeled and formed. For example, an appliance 402-2 can be formed such that it approaches the gingival line 413-2 and does not leave a portion, such as 402-X, of the tooth uncovered.

Figure 5A:
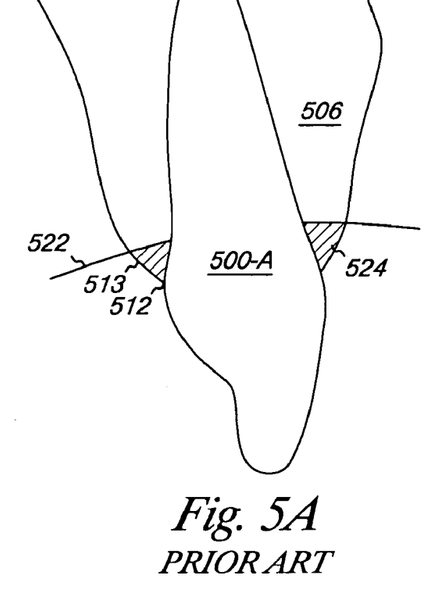
FIG. 5A illustrates a prior art model of a tooth.

FIG. 5A illustrates a prior art model of a tooth. In some dental procedures, periodontal surgery can be used to remove a portion 524 of the gingiva 506 surrounding a tooth 500-A by cutting along a line 522. The portion 524 of the gingiva 506 to be removed is bound by gingival line 513, cut line 522, and the edge of the model of the tooth 500-A as illustrated in FIG. 5A.

Using the gingival point 512 as a reference after a patient undergoes such periodontal surgery, an appliance that only covers the crown of the tooth 500-A up to the gingival point 512 can be formed. The portion of the tooth 500-A exposed by removing portion 524 would not be covered by the appliance.

Figure 5B:
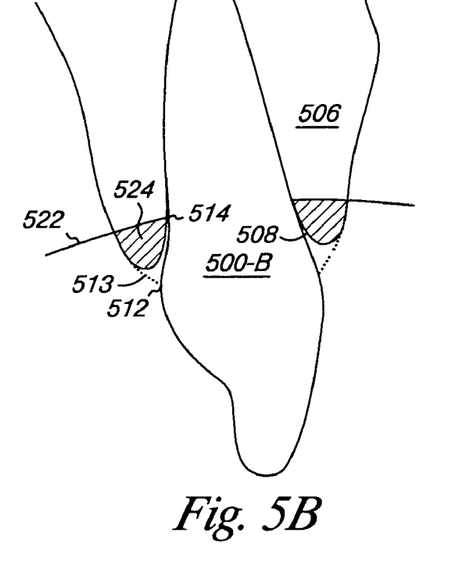
FIG. 5B illustrates a virtual model of a tooth including a simulation of gingival shrinkage from periodontal surgery according to one or more embodiments of the present disclosure.

FIG. 5B illustrates a virtual model of a tooth 500-B including a simulation of gingival shrinkage from periodontal surgery according to one or more embodiments of the present disclosure. The model of tooth 500-B includes a more accurate representation of the gingiva 506 with gingival attachment point 514 and simulated pocket 508. The gingival line 513 and gingival point 512 are illustrated in order to aid comparison between embodiments of the present disclosure and that of FIG. 5A.

The embodiment illustrated in FIG. 5B includes a simulation of periodontal surgery (e.g., a gingivectomy) represented by cut line 522. The simulation can include a portion 524 of the gingiva 506 to be removed from either or both sides of the virtual tooth 500-B.

According one or more embodiments of the present disclosure, the surgery can be simulated without having to adjust the control point. That is, using some previous approaches, gingival point 512 would have to be moved in order to model a proper fit for an appliance.

In contrast, using gingival attachment point 514 as a control point allows the model to adjust for removing portion 524 of the gingiva 506 without changing control points. That is, the gingival crest height adjustment in the virtual dental model (and corresponding dental appliance) can accommodate the change in the gingival contour from the surgical procedure.

At least partially as a result of using the gingival attachment point 514 as a control point, an appliance can be modeled and formed over virtual tooth 500-B up to gingival attachment point 514. Such an appliance can effectively cover the entire exposed crown of the virtual tooth 500-B thereby providing a more aesthetically pleasing appearance and more efficiently functioning device.

In one or more embodiments an expected reduction in gum tissue configuration surrounding a particular tooth can be based on one or more predicted changes to gingival pocket depth. For example, the predicted changes to gingival pocket depth can be due to a course of treatment, among other causes.

Figure 6A:
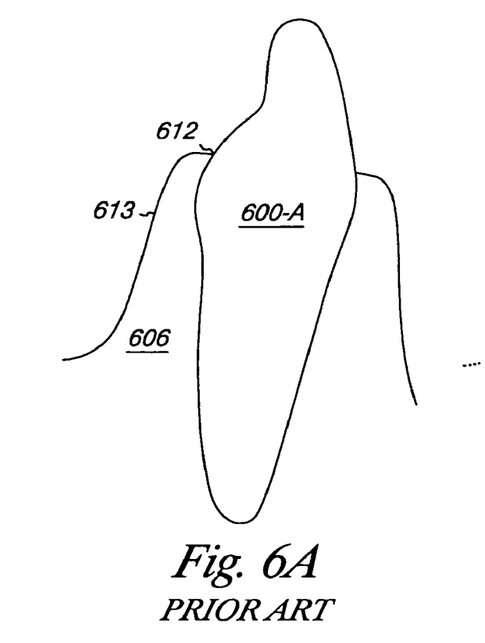
FIG. 6A illustrates a prior art model of a tooth.

FIG. 6A illustrates a prior art model of a tooth including gingival lines. According to some previous approaches, simulating improved oral hygiene (e.g., gingival tissue 606 shrinkage and/or reduction) may not be possible because the gingival point 612 was used as a control point for modeling changes.

Such improved oral hygiene (e.g., from improved brushing and/or flossing, for example, during dental treatment) can yield gingival tissue 606 shrinkage at least partially resulting in changing the contour (e.g., gingival line 613) of the gingiva 606. When the contour of the gingiva 606 changes due to gingival tissue 606 reduction, the location of the point where the gingiva 606 approach the tooth 600-A (e.g., gingival point 612) can move further towards the bottom (e.g., as illustrated in FIG. 6A) of virtual tooth 600-A.

However, according to some previous approaches that use the gingival point 612 as a control point, the gingival point 612 does not move in the model. Therefore, if a patient experiences gingival tissue 606 reduction (e.g., as the result of improved oral hygiene) successive appliances will not cover the entire exposed area of the tooth (e.g., virtual tooth 600-A) because the one or more appliances end at the fixed gingival point 612.

Figure 6B:
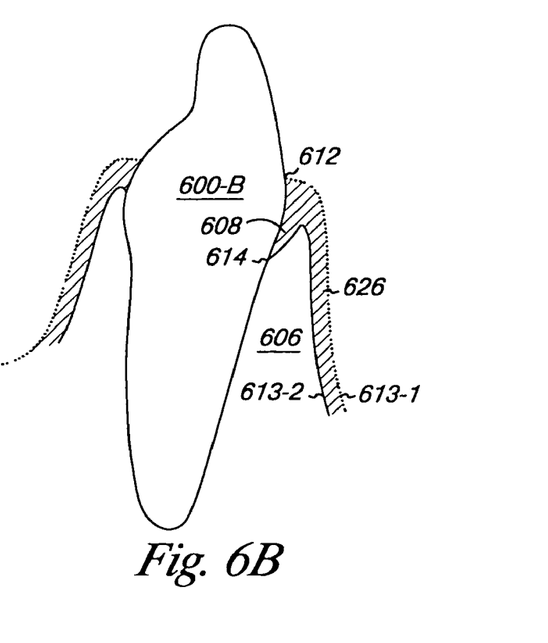
FIG. 6B illustrates a virtual model of a tooth including a simulation of improved oral hygiene according to one or more embodiments of the present disclosure.

FIG. 6B illustrates a virtual model of a tooth 600-B including gingival attachment points 614 and a simulation of improved oral hygiene according to one or more embodiments of the present disclosure. The model of tooth 600-B includes a more accurate representation of the gingiva 606 with gingival attachment point 614 and simulated pocket 608. The first gingival line 613-1 and gingival point 612 are illustrated in order to aid comparison between embodiments of the present disclosure and FIG. 6A.

The embodiment illustrated in FIG. 6B includes a simulation of improved oral hygiene (e.g., reduced gingival tissue) represented by the hashed area between the first gingival line 613-1 and the second gingival line 613-2. The simulation can include a portion 626 of the gingiva 606 that is reduced from either or both sides of the virtual tooth 600-B.

According one or more embodiments of the present disclosure, the gingival tissue shrinkage can be simulated without having to adjust the control point. In such embodiments, using gingival attachment point 614 as a control point can allow the model to adjust for reducing portion 626 of the gingiva 606 without changing control points.

At least partially as a result of using the gingival attachment point 614 as a control point, an appliance can be modeled and formed over virtual tooth 600-B up to the top of the second gingival line 613-2. For example, the virtual model of the crest of the tissue can be programmed to shrink over time without changing the control point. The appliance designed based on the virtual model can effectively cover the entire exposed crown of the virtual tooth 600-B thereby providing a more aesthetically pleasing appearance and more efficiently functioning device, in some instances.

The rate of reduction can be experimentally determined as a function of length of treatment, length of periodontal therapy, type of periodontal therapy, patient age, and patient gender, among others. A model rate of reduction can also be built based on expert opinion (e.g., expert opinion based on studies of a plurality of patients and/or expert opinion of a dental professional based on previous experience with a particular patient).

Figure 7:
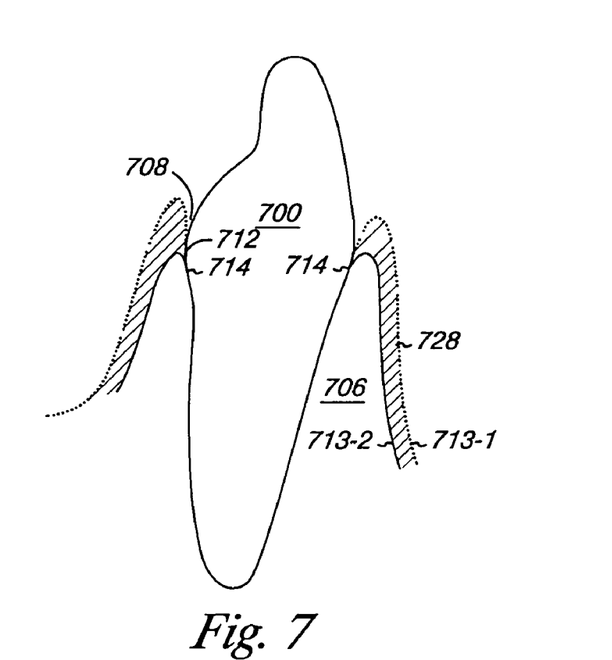
FIG. 7 illustrates a virtual model of a tooth including a simulation of gingival inflammation from worsened oral hygiene according to one or more embodiments of the present disclosure.

FIG. 7 illustrates a virtual model of a tooth including a simulation of gingival inflammation from worsened oral hygiene according to one or more embodiments of the present disclosure. The model of tooth 700 includes a representation of the gingiva 706 with gingival attachment points 714 and simulated pockets 708.

The embodiment illustrated in FIG. 7 includes a simulation of worsened oral hygiene (e.g., gingivitis) represented by the hashed area between the first gingival line 713-1 and the second gingival line 713-2. The simulation can include a portion 728 of the gingiva 706 that is inflamed from either or both sides of the virtual tooth 700. In some instances, the inflammation may be due to tissue compression from adjacent teeth that have moved towards each other during diastema space or extraction space closure, for example.

According one or more embodiments of the present disclosure, the gingival tissue inflammation can be simulated without having to adjust the control point. In such embodiments, using gingival attachment point 714 as a control point allows the model to adjust for inflamed portion 728 of the gingiva 706 without changing control points.

At least partially as a result of using the gingival attachment point 714 as a control point, an appliance can be modeled and formed over virtual tooth 700 up to the top of the second gingival line 713-2. Such an appliance can effectively cover the entire exposed crown of the virtual tooth 700 thereby providing an aesthetically pleasing appearance and more efficiently functioning device, in some instances.

In some embodiments, an expansion (e.g. inflammation) factor to the surface contour of the gingival line 713-1 can be built in to the computing device model without affecting the gingival attachment point 714. The rates of expansion can be determined experimentally as a function of length of treatment, length of periodontal therapy, type of periodontal therapy, patient age, and/or patient gender, among other factors. A model rate of expansion can also be built based on a treatment professional opinion (e.g., an opinion based on studies of a plurality of patients and/or opinion of a treatment professional based on previous experience with a particular patient).

Figure 8:
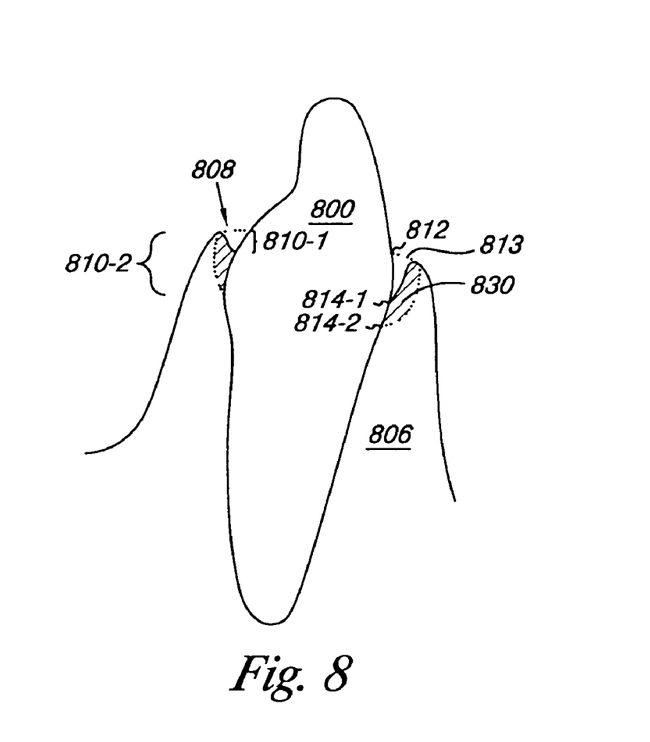
FIG. 8 illustrates a virtual model of a tooth including a simulation of worsened pocket depths according to one or more embodiments of the present disclosure.

FIG. 8 illustrates a virtual model of a tooth including gingival lines, gingival attachment points, and a simulation of worsened pocket depths according to one or more embodiments of the present disclosure. The model of tooth 800 includes a representation of the gingiva 806 with simulated pockets 808 and gingival point 812.

The embodiment illustrated in FIG. 8 includes a simulation of worsened worsened pocket depths (e.g., periodontitis) represented by the hashed area 830 between the first gingival attachment point 814-1 and the second gingival attachment point 814-2. That is, the pocket depth increases from a first depth 810-1 to a second depth 810-2.

According one or more embodiments of the present disclosure, the attachment points (e.g., attachment point 814-1) can be altered at a given rate that can be programmed into the computing device model. The rate can be based on actual historical rates of change to the patient as measured at different times, by statistics, and/or by treatment professional opinion (e.g., opinion based on studies of a plurality of patients and/or opinion of one or more treatment professionals based on previous experience with patients).

In one or more embodiments an expected gum tissue configuration surrounding a particular tooth can be derived based on changes to the gingival line (e.g., line 813 of FIG. 8) and one or more gingival attachment points (e.g., points 814-1 and 814-2). For example, the expected gum tissue configuration surrounding the particular tooth can be based on one or more predicted changes to gingival pocket depth as discussed above.

Figure 9:
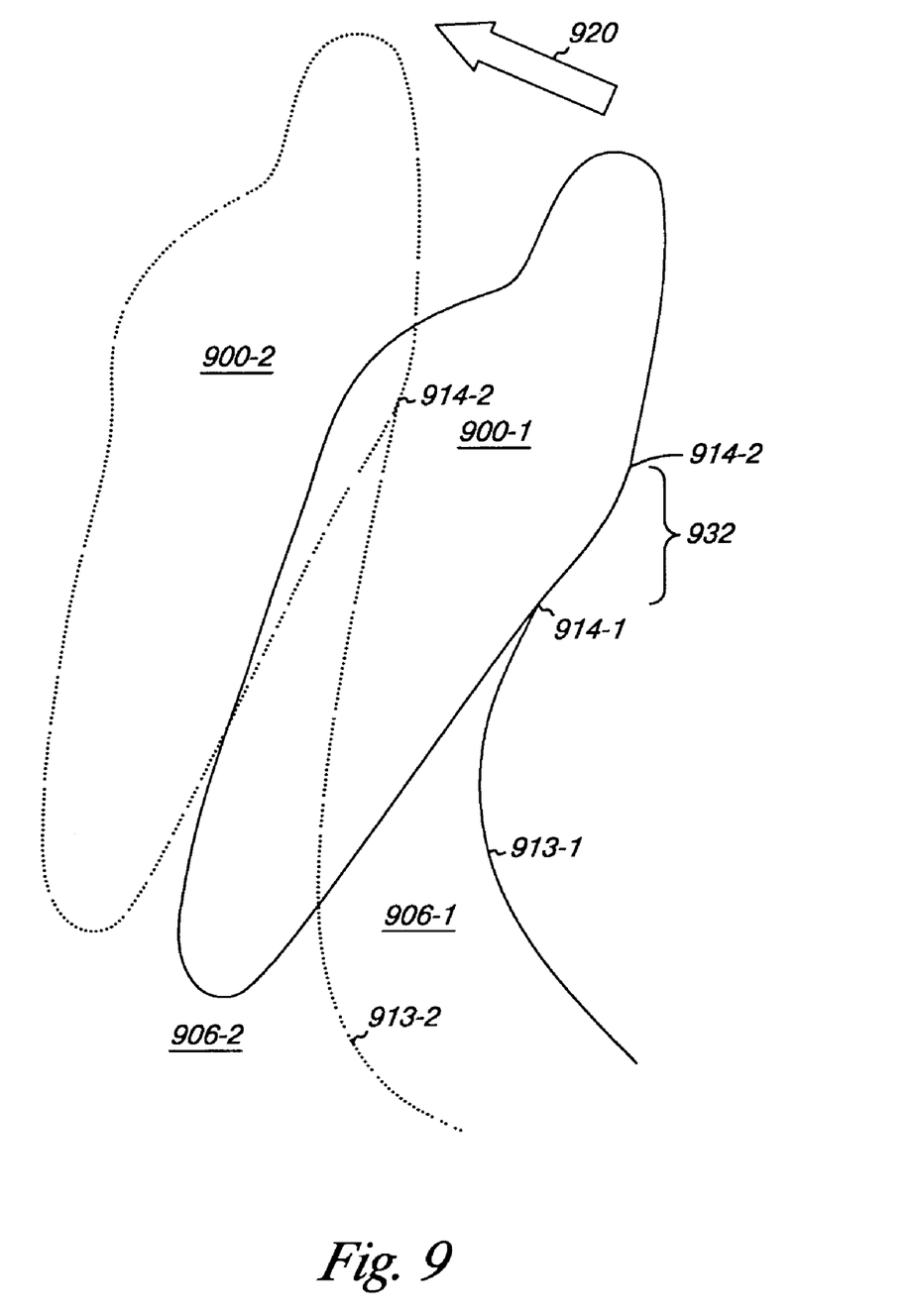
FIG. 9 illustrates a virtual model of a tooth including a simulation of improved positioning of the tooth into the periodontal support structure and a corresponding change in gingival attachment points according to one or more embodiments of the present disclosure.

FIG. 9 illustrates a virtual model of a tooth including a simulation of improved positioning into the periodontal support structure and a corresponding change in gingival attachment points and according to one or more embodiments of the present disclosure. The virtual tooth 900-1 illustrated as a solid line with gingival line 913-1 undergoes a transition 920 to a second position as shown by the virtual tooth 900-2 illustrated as a dotted line with gingival line 913-2.

When an actual tooth is positioned off-centered out of the supporting jaw, the gingival attachment (e.g., attachment 914-1) may not be at the CEJ (e.g., CEJ 217 in FIG. 2). Rather, a defect (e.g., dehiscence) can form due at least partially to the tooth being off-centered with respect to the jaw. For example, a tooth that is buccally positioned (e.g., virtual tooth 900-1) can have a lower attachment (e.g., attachment 914-1) on the tooth, whereas the properly positioned tooth (e.g., virtual tooth 900-2) has an attachment (e.g., attachment 914-2) that is closer to the CEJ.

As the virtual tooth 900-1 transitions 920 into a proper location in the jaw support, the attachment 914-1 can reattach at the CEJ as illustrated by attachment 914-2. Such a transition 920 can be modeled by determining a jaw boundary within which an attachment 914-1 will be present, but outside of which the attachment will be at the intersection between the jaw boundary and the nearest cementum on the virtual tooth. The actual jaw boundary may be determined from an impression of the patient and/or from a direct scan of the patient using structured light and/or x-rays, among other technologies.

In one or more embodiments, one or more gingival attachment points can be first established at a dehiscence of a tooth off centered out of a jaw support for which the gingival pocket depth cannot be directly measured. In some embodiments, the one or more gingival attachment points can be reestablished at the CEJ as the tooth is positioned into the jaw support.

At least partially as a result of the computing device model dynamically adjusting the attachment point to simulate a transition 920, an appliance can be modeled and formed over virtual tooth 900-2 from the cusp of the tooth to the cusp of the second gingival line 913-2. Such an appliance can effectively cover the entire exposed crown of the virtual tooth 900-2 thereby providing an aesthetically pleasing appearance and more efficiently functioning device when an actual appliance is formed according to the model.

In contrast, an appliance formed according to some previous approaches using a static control point (e.g. one placed at attachment point 914-1) could extend from the cusp of the virtual tooth 900-2 to the cusp of gingival line 913-1. Such an appliance used on a tooth that transitioned to a proper location (e.g., virtual tooth 900-2) would extend beyond the cusp of the second gingiva 906-2 to the cusp of the first gingiva 906-1 by an amount, for example, approximately equal to the difference between the cusps 932.

Figure 10:
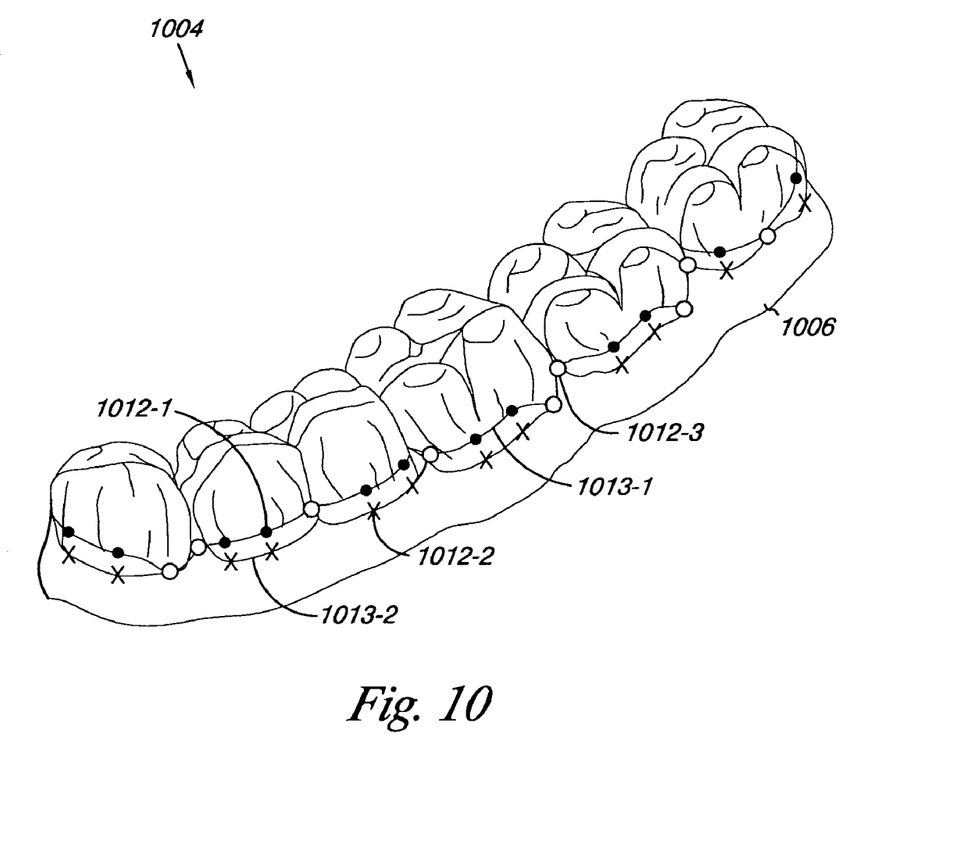
FIG. 10 illustrates a virtual model of several teeth including a simulation of automatic determination of changes to gingival attachment points using various gingival control points according to one or more embodiments of the present disclosure.

FIG. 10 illustrates a virtual model of several teeth including a simulation of automatic determination of changes to gingival attachment points using various gingival control points according to one or more embodiments of the present disclosure. In the embodiment of FIG. 10, the original gingival line prior to treatment 1013-1 is indicated on the model of several teeth 1004. The model also features a line 1013-2 indicating a projected location of where the periodontal tissue is expected to be at the end of treatment, as is also indicated by the level of the gingiva 1006 in the model.

The solid dots (e.g., solid dot 1012-1) represent points on the gingival line at the beginning of treatment. The cross marks (e.g. cross mark 1012-2) represent points on the gingival line at the end of treatment that have changed from the solid dots (e.g., solid dot 1012-1). The hollow dots (e.g., hollow dot 1012-3) represent points on the gingival line at the end of treatment that may not change during treatment.

The virtual model of several teeth 1004 can account for periodontal pockets and gingival attachment at the CEJ in order to determine overall gingival contour. A user (e.g., a treatment professional) can account for the net effect gingival line impact.

In some embodiments an expected gum tissue configuration surrounding a particular tooth can be derived in the model based on changes to the gingival line and one or more gingival attachment points. In one or more embodiments, a digital model can be three-dimensional and include a visual display of the teeth and gums with indications of the gingival line and gingival attachment points.

Figure 11:
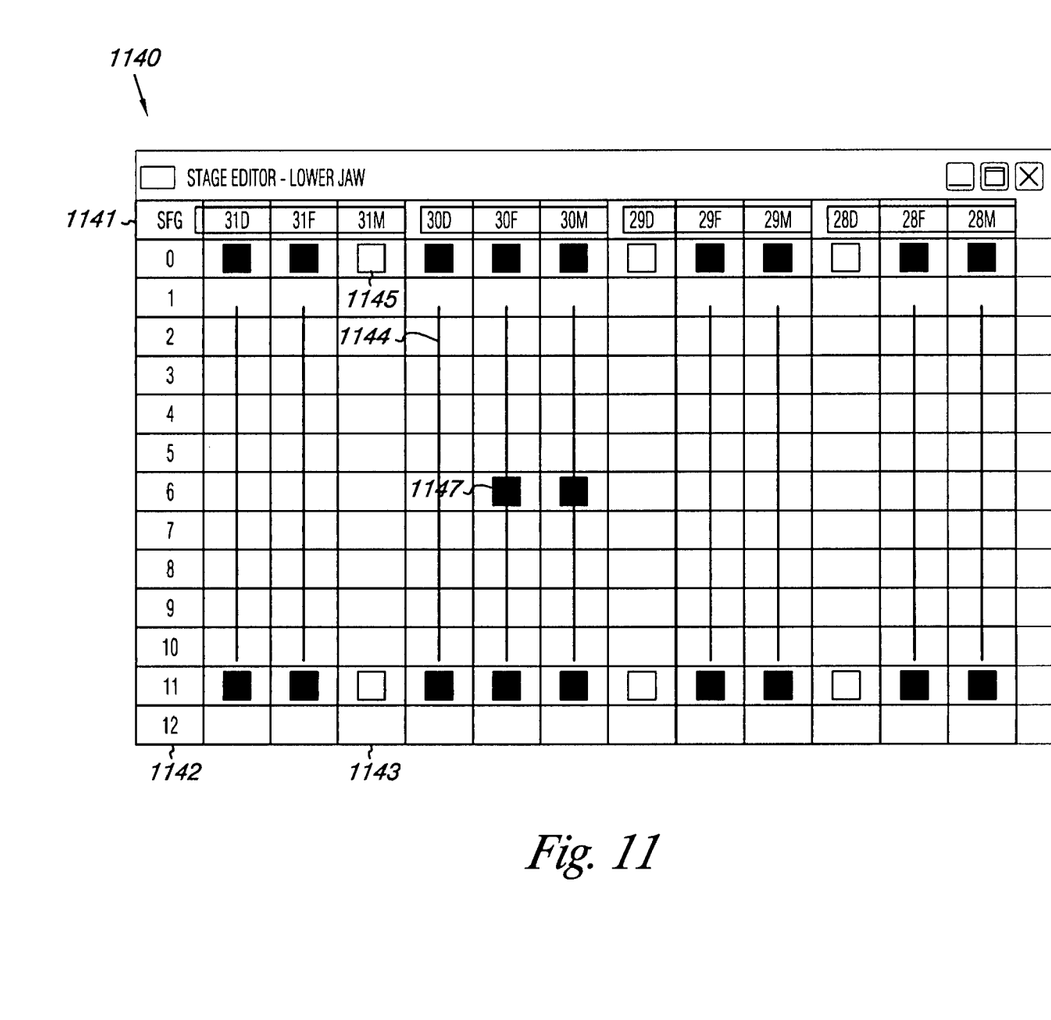
FIG. 11 illustrates a graphical user interface that allows a dental professional to view and edit various gingival control points according to one or more embodiments of the present disclosure.

FIG. 11 illustrates a graphical user interface that allows a dental professional to view and edit various gingival control points according to one or more embodiments of the present disclosure. In the embodiment of FIG. 11, the graphical user interface (GUI) 1140 illustrates a top row 1142 that represents a number of gingival control points for each tooth (e.g., teeth 31, 30, 29, and 28). Although three control points are illustrated for each tooth (e.g., distal, facial, and/or mesial), embodiments are not so limited as more or less control points per tooth may be used in various embodiments.

The first column 1142 indicates up to 13 steps (e.g., from 0-12) in a dental treatment plan (e.g., up to 13 different appliances can be created as a set for a treatment plan). Embodiments are not limited to the specific number of steps illustrated in this example.

In the embodiment of FIG. 11, certain columns are illustrated with a vertical line (e.g., line 1144) running from row 0 to row 11 for particular control points on corresponding teeth. Such a line can indicate that a change in the tissue contour is expected.

In the embodiment of FIG. 11, certain columns are illustrated without a vertical line (e.g., column 1143). Such columns can indicate that no change is expected for the particular control point on the corresponding tooth. Such columns can include an empty box (e.g. box 1145) indicating the same, among other indicator types.

The "speed" with which changes to a particular control point for a particular tooth take place can be indicated, for instance, by the total distance divided by the number of stages over which the gingiva is moving. For example, control point 31D is moving a particular distance (not illustrated) over 12 stages.

The use of "intermediate keyframes" (e.g., keyframe 1147 at stage six for control point 30F) allows varying speeds to be introduced into the treatment plan. For example, the first segment of treatment could adjust control point 30F a first distance over stages 0-6, and over a second (different) distance over stages 6-11 (i.e., at different speeds). One of ordinary skill in the art will appreciate the utility of adjusting different control points at different speeds over the course of a treatment plan.

A method of changing the speed at which a control point is adjusted can be assigned using the GUI 1140. For example, the speed at which a control point is adjusted can be assigned as linear, exponential, logarithmic, and/or parabolic, among others. The formulas for the gingival speed can be determined for various embodiments by statistics and/or treatment professional opinion.

The positions of the final gingival contour (e.g., line 1013-2 in FIG. 10) can be determined by statistics and/or treatment professional opinion and may vary depending on the clinical conditions present. For example, different rates of gingival movement can depend on initial hygiene, type of extraction/exfoliation, and/or type of tooth movement, among others.

Figure 12:
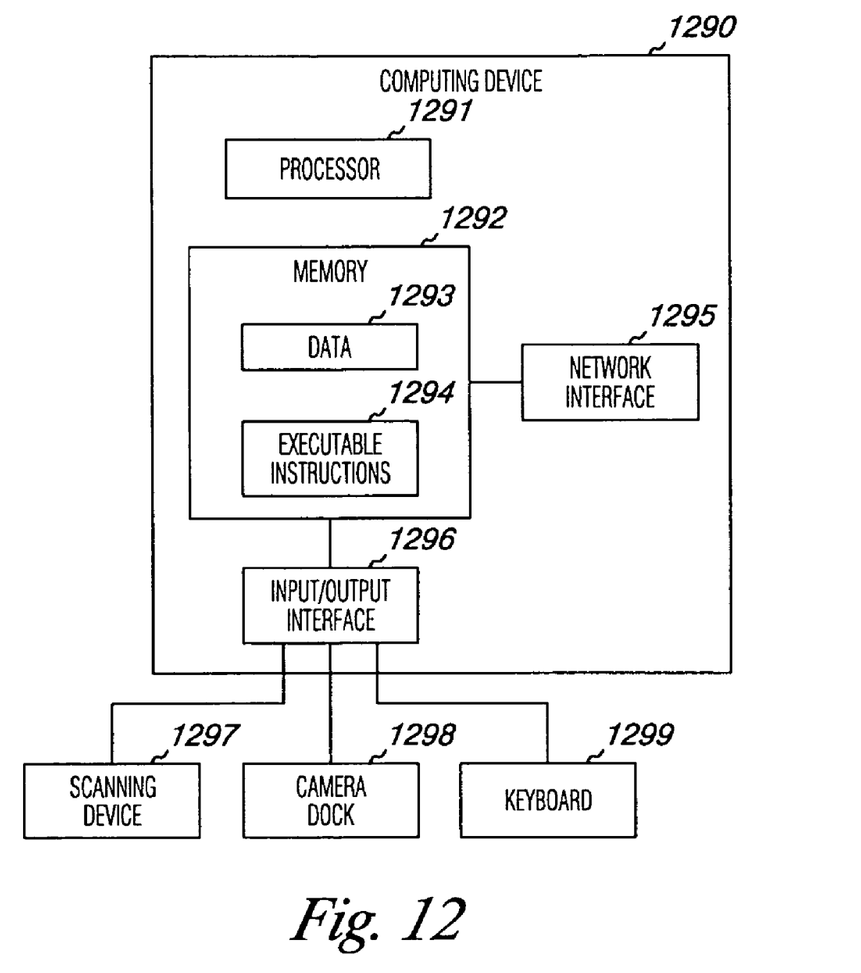
FIG. 12 provides a system for remodeling of the virtual periodontal tissue according to one or more embodiments of the present disclosure.

FIG. 12 provides a system for dynamic remodeling of the virtual periodontal tissue to better accommodate gingival tissue changes by at least establishing in the model a gingival attachment point at the pocket depth from the gingival line. In the system illustrated in FIG. 12, the system includes a computing device 1290 having a processor 1291 and memory 1292. The memory can include various types of information including data 1293 and executable instructions 1294 as discussed herein.

Memory and/or the processor may be located on the device 1290 or off the device in some embodiments. As such, as illustrated in the embodiment of FIG. 12, a system can include a network interface 1295. Such an interface can allow for processing on another networked computing device or such devices can be used to obtain information about the patient or executable instructions for use with various embodiments provided herein.

As illustrated in the embodiment of FIG. 12, a system can include one or more input and/or output interfaces 1296. Such interfaces can be used to connect the computing device with one or more input or output devices.

For example, in the embodiment illustrated in FIG. 12, the system includes connectivity to a scanning device 1297, a camera dock 1298, and a keyboard 1299. Periodontal pocket depth measurements may be captured with an electronic periodontal probe input system, e.g., a Florida Probe, which can be connected to a computer, among other types of measuring device types.

Such connectivity can allow for the input and/or output of image information (e.g., scanned images or digital pictures, etc.) or instructions (e.g., input via keyboard) among other types of information. Although some embodiments may be distributed among various computing devices within one or more networks, such systems as illustrated in FIG. 12 can be beneficial in allowing for the capture, calculation, and/or analysis of information discussed herein.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A computing device-implemented method for modeling gingiva, the method comprising:
    scanning a patient's teeth and gums, or a physical model thereof, to obtain location data;
    developing a digital model via a computing device, where the model represents a dentition and gingiva from the location data;
    defining in the model a gingival line at an intersection between at least one tooth and at least a portion of its surrounding gums;
    measuring a gingival pocket depth at a number of reference locations;
    establishing in the model one or more gingival attachment points at the pocket depth from the gingival line; and
    deriving in the model an expected gum tissue configuration surrounding a particular tooth based on changes to the gingival line and one or more gingival attachment points; and
    deriving a cut line for one or more dental position adjustment appliances, where the cut line is associated with a dynamically modeled gingival line.

2. The method of claim 1, wherein the method includes deriving in the model an expected deformation of gum tissue surrounding a particular tooth based on force applied to the gum tissue through the one or more gingival attachment points.

3. The method of claim 2, wherein the force applied through the one or more gingival attachment points is transmitted from a positioning force applied to the particular tooth.

4. The method of claim 3, wherein the force applied to the particular tooth is a virtual positioning force from a simulated orthodontic treatment plan.

5. The method of claim 1, wherein the method includes deriving in the model an expected deformation of gum tissue surrounding a particular tooth based on one or more tension forces within the gum tissue.

6. The method of claim 1, wherein the expected gum tissue configuration surrounding a particular tooth is based on one or more predicted changes to gingival pocket depth.

7. The method of claim 6, wherein the at least one of the predicted changes to gingival pocket depth is due to a course of treatment.

8. The method of claim 7, wherein the course of treatment is selected from a group including: periodontal surgery, gingivectomy, improved oral hygiene activities, and worsened oral hygiene activities.

9. The method of claim 6, wherein at least one of the predicted changes to gingival pocket depth is attributable to changes in dental health.

10. The method of claim 9, wherein at least one of the changes in dental health is selected from a group including: gingivitis, tooth eruption, tissue compression, and periodontitis.

11. The method of claim 1, wherein the method further includes establishing at least one gingival attachment point at a cementoenamel junction of a tooth for which the gingival pocket depth cannot be directly measured.

12. The method of claim 1, wherein the method further includes establishing at least one gingival attachment point at a dehiscence of a tooth off centered out of a jaw support for which the gingival pocket depth cannot be directly measured.

13. The method of claim 12, wherein the method further includes re-establishing the at least one gingival attachment point at a cementoenamel junction as the tooth is positioned into the jaw support.

14. The method of claim 1, wherein measuring includes deriving depth data from digital bone level information of a CT scan.

15. The method of claim 1, wherein developing the model representing the gingiva includes assigning a control point to the one or more gingival attachment points per tooth.

16. The method of claim 15, wherein developing the model representing the gingiva includes adjusting a speed of movement from a first position to one or more other positions over time of one or more control points according to a positioning scheme selected from a group including: linear, exponential, logarithmic, and parabolic.

17. The method of claim 1, wherein the digital model is three-dimensional and includes a visual display of the teeth and gums with indications of the one or more gingival line and gingival attachment points.

18. A computing system, comprising:
    a processor;
    a data storage device communicatively coupled to the processor, the data storage device containing executable instructions to cause a computing device to:
    receive location data obtained from a scan of a patient's teeth and gums, or a physical model thereof;
    develop a digital model representing a dentition and gingiva from the location data;
    define in the model a gingival line at an intersection between at least one tooth and at least a portion of its surrounding gums;
    receive distance data obtained from a measurement of gingival pocket depth at a number of reference locations;
    establish in the model one or more gingival attachment points at the pocket depth from the gingival line; and
    deriving in the model an expected gum tissue configuration surrounding a particular tooth based on changes to the gingival line and one or more gingival attachment points; and
    deriving a cut line for one or more dental position adjustment appliances, where the cut line is associated with a dynamically modeled gingival line.

19. A non-transitory computing device readable medium having executable instructions which can be executed by a processor to cause a computing device to perform a method, comprising:

receiving location data obtained from a scan of a patient's teeth and gums, or a physical model thereof;

developing a digital model representing a dentition and gingiva from the location data;

defining in the model a gingival line at an intersection between at least one tooth and at least a portion of its surrounding gums;

receiving distance data obtained from a measurement of gingival pocket depth at a number of reference locations;

establishing in the model one or more gingival attachment points at the pocket depth from the gingival line; and deriving in the model an expected gum tissue configuration surrounding a particular tooth based on changes to the gingival line and one or more gingival attachment points; and deriving a cut line for one or more dental position adjustment appliances, where the cut line is associated with a dynamically modeled gingival line.

* * * * *